US007712956B2

(12) United States Patent
Richner et al.

(10) Patent No.: US 7,712,956 B2
(45) Date of Patent: May 11, 2010

(54) METHOD AND DEVICE FOR DETERMINING SPECIFIC HEAT CAPACITY

(75) Inventors: Gilles Richner, Zurich (CH); Konrad Hungerbuehler, Wintersingen (CH); Benedikt Schenker, Wuerenlingen (CH)

(73) Assignee: Mettler-Toledo AG, Greifensee (CH)

( * ) Notice: Subject to any disclaimer, the term of this patent is extended or adjusted under 35 U.S.C. 154(b) by 0 days.

(21) Appl. No.: 12/372,003

(22) Filed: Feb. 17, 2009

(65) Prior Publication Data

US 2009/0154520 A1 Jun. 18, 2009

Related U.S. Application Data

(63) Continuation of application No. PCT/EP2007/007143, filed on Aug. 13, 2007.

(30) Foreign Application Priority Data

Aug. 15, 2006 (EP) ................................. 06016978

(51) Int. Cl.
*G01N 25/20* (2006.01)
*G01K 17/00* (2006.01)

(52) U.S. Cl. ............................. 374/43; 374/33; 422/51

(58) Field of Classification Search .................. 374/43, 374/33; 422/51
See application file for complete search history.

(56) References Cited

U.S. PATENT DOCUMENTS 4,383,438 A * 5/1983 Eaton ........................ 73/61.62
4,456,389 A * 6/1984 Regenass et al. .............. 374/31
4,963,499 A 10/1990 Stockton et al.
6,071,008 A 6/2000 Hatta et al.
6,953,280 B2 10/2005 Fischer et al.
7,220,050 B2 5/2007 Esprimont et al.
2003/0026736 A1 * 2/2003 Hajduk et al. ............ 422/82.12

FOREIGN PATENT DOCUMENTS

EP 0647839 A1 4/1995

OTHER PUBLICATIONS

Zogg, A. et al., "A New Small-Scale Reaction Calorimeter That Combines the Principles of Power Compensation and Heat Balance", Ind. Eng. Chem. Res., 2003, pp. 767-776, vol. 42, No. 4.
Zogg, A. et al., "Isothermal reaction calorimetry as a tool for kinetic analysis", Thermochimica Acta, 2004, pp. 1-17, vol. 419.

* cited by examiner

*Primary Examiner*—Gail Verbitsky
*Assistant Examiner*—Mirellys Jagan
(74) *Attorney, Agent, or Firm*—Standley Law Group LLP

(57) ABSTRACT

The specific heat capacity ($c_p$) of a medium is determined using a calorimeter with a reactor (1), a stirrer (3), a first thermostat for providing an inner heat balance, a second thermostat, means for providing an outer heat balance and a central control unit (35). The method uses the steps of: applying a modulated energy profile to the medium, inside the reactor (1), under near isothermal conditions; monitoring the resulting energy changes of: the medium, the reactor (1), the first thermostat, the second thermostat and/or the outer heat balance means as a function of time; determining the respective inner and outer heat balances independently from each other at predefined time intervals; and calculating the overall heat transfer coefficient (UA) and the specific heat capacity of the medium ($c_p$) simultaneously and independently from each other as a function of time from the inner and outer heat balances.

17 Claims, 5 Drawing Sheets

METHOD AND DEVICE FOR DETERMINING SPECIFIC HEAT CAPACITY

CROSS-REFERENCE TO RELATED APPLICATIONS

This application is a continuation under 35 USC §120 of PCT/EP2007/007143, filed 13 Aug. 2007, which is in turn entitled to benefit of a right of priority under 35 USC §119 from European patent application 06 01 6978.6, filed 15 Aug. 2006, the contents of each of which is incorporated by reference as if fully recited herein.

TECHNICAL FIELD

The invention concerns the determination of the specific heat capacity $c_p$ of a sample or medium arranged inside a temperature controlled reactor, such as a calorimeter reactor.

BACKGROUND OF THE ART

The heat capacity $C_p$ is a thermo-physical property. The heat capacity of a medium as well as the heat capacities of different parts of a setup has to be known for scale-up processes, reactor design as well as for safety assessments. The heat capacity of a medium or of a sample, e.g. a fluid, is often determined with calorimetric methods, which comprise the application of a specific temperature profile, such as a temperature ramp, to a medium inside a reactor. The temperature profile is usually generated and controlled by a temperature-controlling system, which interacts with the reactor.

Calorimetric experiments are easy to conduct but harbor several drawbacks concerning the accuracy of the obtained data. The accuracy is influenced by the calibration procedure, the instrumental noise and heat losses, e.g. through the reactor and its temperature-controlling system. Additionally, such experiments can be very time consuming. The accuracy of the determination of the heat capacity $C_p$ can be enhanced by utilizing large temperature differences, but as the heat capacity $C_p$ depends on the temperature small temperature differences would be sufficient to obtain accurate data.

A common, but time consuming technique for the determination of the heat capacity $C_p$ is the differential scanning calorimetry (DSC), where a temperature difference between a sample and a reference is measured as a function of time, while a temperature profile is applied to the sample and the reference. This technique requires the individual preparation of each sample. Additionally, inhomogenities can occur in the sample, as this is placed in a small cup without stirring. These inhomogenities can have a negative impact on the experimental results.

A comparable technique for the determination of an absolute value of the heat capacity on a bigger scale has been disclosed in U.S. Pat. No. 6,071,008 A, where a stainless steel tube is arranged in a thermal bath which temperature can be controlled electrically.

European published application EP 0 647 839 A1 discloses the determination of the global heat transfer coefficient in a chemical reactor while a forced temperature oscillation is applied. The reactor is a classic double walled reactor with a thermostat comprising a heat carrier, such as a temperature controlled jacket or hollow coil, which is in contact with the reactor, filled with a heat-transfer medium and interacting with a heating/cooling unit such as a heat exchanger. This technique is also prone to inhomogenities and in particular to local inhomogenities in the sample, which have a negative impact on the results. Especially, the precise and timely control of the thermostat presents a difficulty, as some of the common heat carriers show a delayed reaction on temperature changes. The heat flow through the reactor is generally determined via the temperature difference between the temperature inside the reactor and the temperature of thermostat in particular of the heat carrier.

Therefore, the object of this invention is the development of a method for a fast and accurate determination of the heat capacity and the overall heat coefficient independent from each other, which overcomes the drawbacks of the prior art, and of a calorimeter for performing said method.

SUMMARY

A method for determining the specific heat capacity of a medium and the overall heat coefficient with a calorimeter, wherein said calorimeter comprises a reactor, a stirrer, a first thermostat for providing an inner heat balance, a second thermostat, means for providing an outer heat balance and a central control unit. The method comprises the following steps of applying a modulated energy profile to the medium which is arranged inside the reactor under near isothermal conditions, monitoring the resulting energy changes of the medium, the reactor, the first thermostat, the second thermostat and/or said means for providing an outer heat balance as a function of time. Further, the method comprises the steps of determining at least the inner heat balance and the outer heat balance at predefined time intervals, calculating the overall heat transfer coefficient UA and the specific heat capacity of the medium $c_p$ simultaneously and independently from each other as a function of time from the inner and outer heat balance.

The term near isothermal refers to the fact, that the medium is maintained at isothermal conditions as long as no modulated energy profile is applied and as the chosen amplitude for the modulated energy profile is very small the system is only slightly disturbed and still behaves nearly isothermally when the modulation is applied. The calorimeter comprises at least two thermostats and can preferably be operated by a combination of heat flow and power compensation principles. This combination is very advantageous and allows the independent determination of an inner and an outer heat balance. The inner heat balance of the reactor and the outer heat balance related to the means for providing the outer heat balance can be determined independently from each other. Therefore, it is possible to determine the overall heat transfer coefficient UA directly and independently from the specific heat capacity of the medium $c_p$ without relying on any calibration. The overall heat transfer coefficient UA as well as the specific heat capacity of the medium $c_p$ can be determined continuously throughout an experiment and even while performing a chemical or physical reaction. The determination of UA and $c_p$ can, if desired, be performed continuously or at predefined time intervals which allows to monitor changes of the overall heat transfer coefficient UA as well as of the total heat capacity of the medium $C_{p,m}$. Furthermore, the medium under investigation can be stirred continuously by a stirrer arranged in the reactor in order to provide a homogeneous mixed medium as well as a homogeneous heat and/or energy distribution in the medium which enhances the accuracy of the measuring results.

The term medium should be understood as any kind of material, a pure substance, a reaction mixture or a type of sample with different and/or changing compositions, e.g. through adding other substances in order to perform a chemical reaction.

The modulated energy profile can be generated by an energy modulation superimposed on the signal of the first or inner thermostat, especially when said first thermostat shows a fast reaction to energy changes and is able to transfer the modulation directly to the medium.

In a further embodiment the modulated energy profile can be generated by an energy modulation superimposed on the signal of a third or intermediate thermostat as means for providing an outer heat balance. Said third thermostat can be thermally connected with the second thermostat.

In another embodiment the outer heat balance or more precisely UA can be determined by an array of heat flux sensors arranged in the reactor and acting as means for providing the outer heat balance.

Depending on the calorimeter, its setup and its adaptable parameters the medium can be subjected to a modulated energy profile either in form of a modulated power profile, a modulated heat flow profile or a modulated temperature profile for either the first or, if applicable, the third thermostat. The modulated energy can originate for example from a modulated electrical energy, such as an electrical heater, from a modulated heat flow, e.g. of a temperature-controlled medium or from modulated radiation energy.

When the modulated energy profile is applied to the medium, it also influences other components of the calorimeter, which start to exhibit a similar modulation as answer to the modulation applied to the medium. These resulting energy changes relating to the medium and/or any of the thermostats can be determined directly and/or indirectly by at least one temperature sensor, at least one power meter and/or at least one heat flow sensor. Preferably the resulting energy changes of each component are determined separately by one or by a plurality of the mentioned devices or a combination of said devices. The determination of the heat capacity relies on heat or power values, which can be easily derived from temperature values or be directly measured by heat flow sensors.

For a reliable and exact determination of the total heat capacity of the medium inside the reactor the phase and/or the amplitude of the resulting energy changes have to be monitored. Preferably the amplitude and the phase of all measured energies are monitored.

The modulation of the modulated energy profile can be for example a periodic modulation or a stochastic modulation and can be selected in accordance with the calorimeter in use. The heat capacity of the medium relies amongst other data on the knowledge of the exact form of modulation, which can be incorporated in the mathematical method used to perform said determination. The modulation introduces small changes, in particular small temperature changes into the system. Said changes should be large enough to allow a very exact determination of the specific heat capacity of the medium $c_p$, given the inevitable stochastic noise in the measured signals, and on the other hand small enough so that the temperature dependent properties of the medium under investigation, like $C_p$, rate of reaction or viscosity, do not significantly change.

The modulation can be for example a periodic sinusoidal modulation or a rectangular modulation. It would also be possible to utilize a single pulse or multiple pulses having the same or different amplitudes. Even a ramp function or other types of stochastic or periodic modulation can be utilized. All the modulations described as well as other types known in the art can introduce one or more small temporary disturbance into the calorimetric systems. With the method of the invention the specific heat and the overall heat coefficient can be determined from information about the input modulation and the data obtained from the disturbed calorimeter system.

Preferably, the first thermostat comprises a compensation heater and is controlled in order to compensate for the heat provided by the second and/or the third thermostat and/or for the heat provided by the medium. For the undisturbed system the first thermostat is regulated or controlled to maintain isothermal conditions. While a modulation is applied to the system, in particular to the medium, the first thermostat can be controlled in order to maintain near isothermal conditions.

The first thermostat, in particular a compensation heater, can be arranged inside the reactor in direct contact with the medium. In that case, in particular when the first thermostat has short response times, it is advantageous to superimpose the energy provided by the first thermostat with the modulated energy profile.

According to a preferred embodiment, the modulated energy profile arises from a temperature and/or a heat modulation, which can be applied to the medium by the electric compensation heater, which is in direct contact with the medium. Said compensation heater can apply an oscillating heating power to the medium. Depending on the means to provide an outer heater balance, the heat capacity of the medium and the overall heat transfer coefficient can be independently calculated from the measurements of the heating and cooling power of the first thermostat, the temperature of the reactor and/or of the heat carrier as well as the heating and cooling power of the third thermostat or the power transferred through the reactor wall determined by an array of heat flux sensors.

The invention allows the determination of the specific heat capacity of the medium and of the overall heat transfer coefficient with great accuracy continuously and independently from each other throughout an experiment without the need of further equipment and/or sampling procedures.

A calorimeter utilizable for the determination of the specific heat capacity of a medium and of the overall heat transfer coefficient comprises a reactor, a first thermostat for providing an inner heat balance, a second thermostat, means for providing an outer heat balance, a stirrer arranged inside the reactor and a control unit. The first thermostat and/or said means for providing an outer heat balance are designed to provide a modulated energy profile to the medium. The control unit comprises a program with an algorithm to monitor the resulting energy changes of the medium, the reactor, the first thermostat, the second thermostat and/or said means for providing an outer heat balance as a function of time. Said program is designed to determine an inner and an outer heat balance independently from each other. The program is further designed to simultaneously and independently determine the specific heat capacity of the medium and the overall heat transfer coefficient as a function of time.

The first thermostat comprises a compensation heater, a first temperature sensor arranged inside the reactor and a first controller.

The means for providing an outer heat balance can comprise a third thermostat, which is thermally connected to the second thermostat and which comprises a third controller, a heating/cooling unit, a solid heat carrier, which is in thermal contact with the reactor, and a second temperature sensor for measuring the temperature inside the heat carrier. Preferably the solid heat carrier is a solid metal jacket or a solid coil surrounding the reactor. The solid heat carrier can be heated or cooled directly e.g. electrically. The third thermostat can provide the modulated energy profile to the medium.

The heating/cooling unit of the third thermostat can be designed as one or more Peltier elements interacting with the second thermostat, e.g. a heat exchanger.

In another embodiment the means for providing an outer heat balance comprise an array of at least three heat flux sensors. Preferably the array is a linear one. The heat flux sensors are arranged on the inside of the reactor in contact with the reactor wall. The array of heat flux sensors is partially immersed in the medium arranged inside the reactor. Instead of three distinctive heat flux sensor a linear or two-dimensional array of sensors can be used. A similar arrangement of heat flux sensors is disclosed in U.S. Pat. No. 7,220,050 B2 for the determination of the fluid or medium level inside a reactor.

The invention is also directed to a computer program, which is designed to calculate the overall heat coefficient and the heat capacity of a medium from data obtained while applying the method of invention to a medium arranged in a calorimeter, wherein said calorimeter is adapted to provide an inner heat balance and an outer heat balance, which are independent of each other.

BRIEF DESCRIPTION OF THE DRAWINGS

The method of the invention as well as a calorimeter which can be utilized for the determination of the specific heat capacity of a medium are described in detail below by means of examples and by the following figures.

DETAILED DESCRIPTION

Figure 1B:
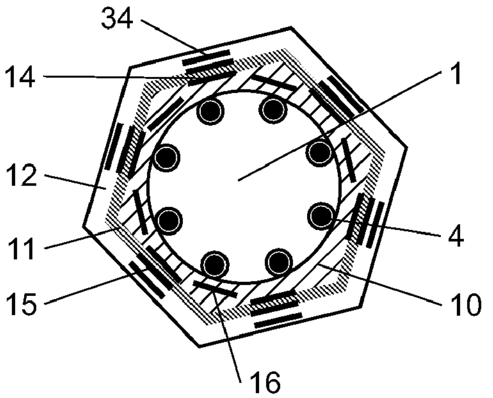
FIGS. 1A and 1B show, respectively, in cross sectional and top views, a calorimeter with a first thermostat, a second thermostat and a third thermostat as means for providing an outer heat balance.
Figure 1A:
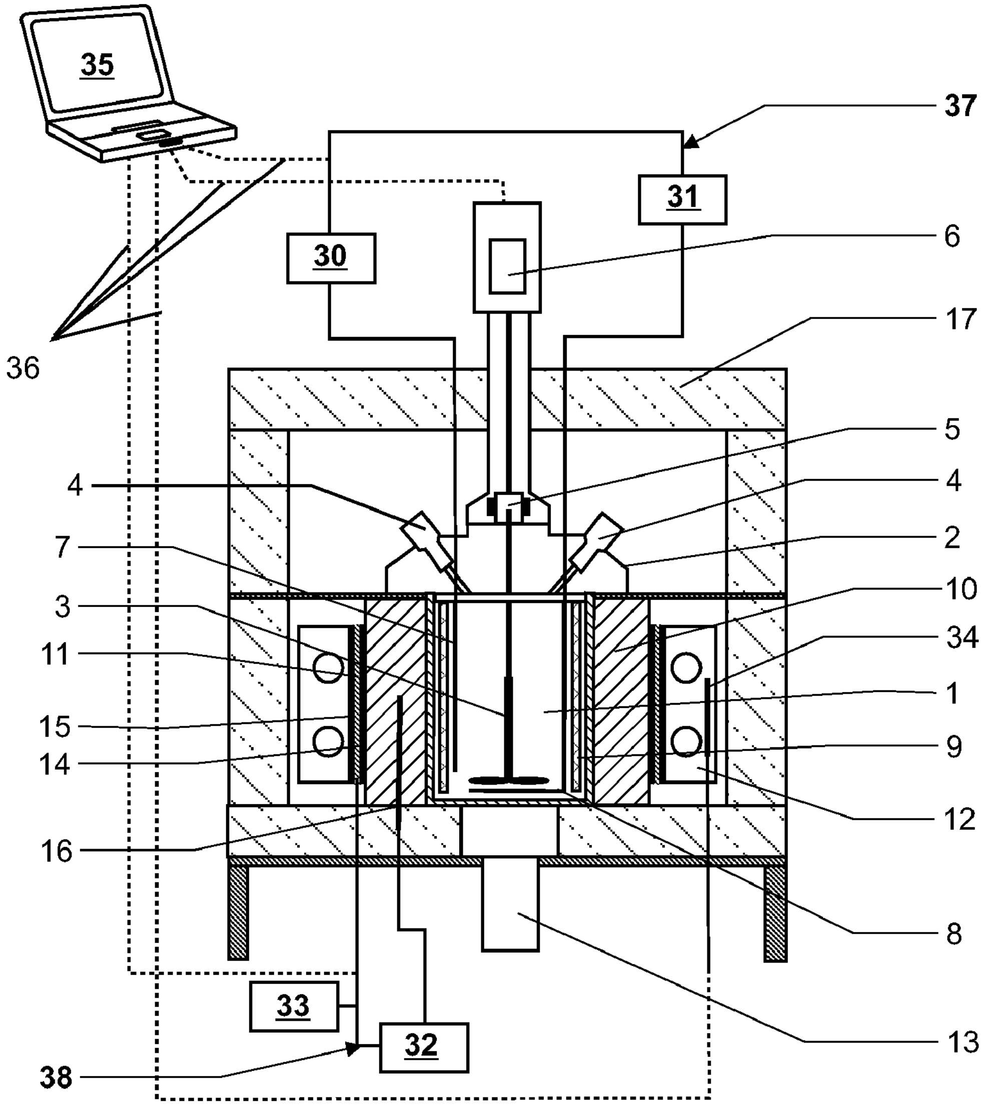

FIG. 1A shows a cross section and FIG. 1B shows a top view of a calorimeter capable to perform the method of the invention. Said calorimeter combines the methods of power compensation and heat flow by utilizing a first thermostat with a compensation heater 8 in addition to a third thermostat with a solid heat carrier provided in form of a thermoelectrically controlled metal jacket 10. Said calorimeter is designed for experiments under isothermal and near isothermal conditions. A calorimeter with a similar design for the second and third thermostat is disclosed in EP 1 184 649 A1.

The calorimeter shown in FIG. 1A comprises a reactor 1 with a removable lid 2. Inside the reactor 1 a stirrer 3 is arranged for stirring a medium therein (not shown here). The stirrer 3 is coupled via a magnetic coupling 5 to a stirrer drive 6. For introducing the medium, feeding further reactants to the medium and/or introducing further instrumentation, such as sensors or an endoscope the lid 2 is equipped with several ports 4.

For performing the method of the invention the calorimeter is at least equipped with a first temperature sensor 7 for measuring the temperature $T_r$ of the medium inside the reactor 1 and a compensation heater 8 for maintaining isothermal conditions and/or for applying a modulated energy profile to the medium. The compensation heater 8 and the first temperature sensor 7, together with a temperature controller 30 and a power output meter 31 connected through a first control loop 37 constitute the first thermostat, which is also referred to as inner thermostat. The interior reactor temperature $T_r$ can be controlled and/or modulated with this first thermostat. The electrical energy of the compensation heater 8 that is required to control the temperature $T_r$ is recorded as a heat signal $q_{comp}$ during a measurement.

The ports 4 also allow the attachment of different devices to the reactor and/or the introduction of different devices into the reactor 1, such as a pressure sensor, an endoscope, a temperature sensor, a heat flow sensor and/or an overpressure valve. The design of the ports 4 can vary due to their intended use. At the bottom of the reactor 1 an optical sensor 13, e.g. an infrared ATR sensor, is arranged. Baffles 9 are arranged inside the reactor 1 for an optimal thorough mixing of the medium.

The metal jacket 10 surrounding the reactor 1, e.g. a copper jacket or copper block, has a symmetric design. The temperature of the metal jacket 10 is controlled by Peltier elements 11, which are connected in a thermally conducting manner to the metal jacket 10 as well as to a second thermostat, such as a heat exchanger 12. The third or intermediate thermostat comprises the metal jacket 10 and the Peltier elements 11. Preferably at least one Peltier element 11 is located on each outer surface of the metal jacket 10 between said jacket 10 and the heat exchanger 12. The Peltier elements 11 together with the heat-exchanger 12 constitute a heating/cooling system for controlling the temperature of the metal jacket.

The temperature $T_J$ of the metal jacket 10 is monitored by a second temperature sensor 16. Additionally, the temperature at the internal face as well as that at the external face of each Peltier element 11 is determined by separate third and fourth temperature sensors 14, 15. Preferably each Peltier element 11 is provided with separate third and fourth temperature sensors 14, 15. The arrangement of the second, third and fourth temperature sensors 14, 15, 16 is shown schematically in FIG. 1B representing a top view of the calorimeter.

The temperature of the heat exchanger 12 or second thermostat does not need to be controlled. This is unnecessary as the Peltier elements 11 are capable of adjusting to positive and/or negative temperature differences with regard to the temperature of the heat exchanger 12. The only requirement for the heat exchanger 12 is that it must provide a sufficiently large cooling capacity and that temperature fluctuations during an experiment should be below or around approximately 2° C. The temperature or the heat from the heat exchanger 12 is measured with an additional fifth temperature or heat flow sensor 34.

The temperature of the metal jacket 10 is controlled by a second control loop 38, which is also comprised in the third thermostat. This control loop 38 comprises at least one temperature sensor 16 that measures the temperature of the metal jacket 10 and a temperature controller 32. The controller 32 is connected to a power output meter 33, as well as to the Peltier elements 11. The metal jacket 10 has due to its inertness a better temperature control than a common jacket filled with a heat transfer medium.

The calorimeter also comprises a central control unit 35 preferably designed to control the whole setup as well as the data acquisition and its evaluation. The control unit 35 is represented in FIG. 1A by a computer and the connections or conduits 36 between the different parts of the calorimeter and the control unit 35 in FIG. 1A are only indicated for a few parts of the calorimeter. The control unit 35 can either be an internal unit or as shown here an external unit. The control unit 35 comprises computing means and a program with an algorithm to perform the method of the invention. The control unit further comprises means to control the calorimeter as well as means to obtain and store any sensor data. Suitable control units 35 are generally well known and are therefore not described in detail here.

To maintain isothermal or near isothermal conditions, as well as to avoid unnecessary energy losses and to mitigate the impact on the measurement under changing environmental conditions the reactor 1, the lid 2, the metal jacket 10, the Peltier elements 11 and the heat exchanger 12 are surrounded by a thermal insulation 17.

In addition to the output signal of the compensation heater 8 a second thermal signal can be measured with said calorimeter. This second thermal signal relates to the output of the Peltier elements 11 required for regulating the temperature of the metal jacket 10. The temperature of the metal jacket 10 is controlled either isothermally or during a modulation near isothermally. Under isothermal conditions the two measured electrical outputs can be described as follows: The output of the compensation heater 8 which is required to keep the temperature of the medium constant, contains the sum of the reaction output and heat flow through the interior reactor wall. The output of the Peltier elements 11 that is required to keep the temperature of the metal jacket 10 constant, is related to the heat flow through the interior reactor wall and is independent from the reaction output. This is essential for the determination of two independent heat balances.

FIG. 1B shows a top view of the calorimeter of FIG. 1A. The same reference numerals refer to the same elements. In FIG. 1B the lateral relation between the reactor 1, the jacket 10, the Peltier Elements 11, the heat exchanger 12 and the different sensors 14, 15, 16, 34 is shown as well as the preferred hexagonal shape of said calorimeter and the position of the different ports 4.

The experimental separation of the two heat flows and therefore also that of the two heat balances mentioned above allows the determination of the heat transfer coefficient and the heat capacity of the medium independently from each other with the method described in detail below. This is possible, because changes in the heat transmission of the reactor wall can be measured and taken into account in the heat balances. The measuring principle of the calorimeter is based on the compensation heater 8 and the heat flow measurement by means of Peltier elements 11.

Due to the direct heating or cooling of the metal jacket 10 and the interior of the reactor 1 by means of electrical heating or cooling elements, respectively, the regulation of the corresponding temperatures can be easily accomplished. The total volume of the equipment is for example in the order of 0.5 m×0.2 m×0.2 m for reactors with a volume of about 250 ml or less. Even a plurality of such calorimeters can easily be arranged in one fume cupboard. Furthermore, the heat exchanger 12 can be designed in such a way that it can interact with allowing the operation of a plurality of calorimeters at the same time, so that parallel operations become possible. With parallel operations of this type, a plurality of reactors is connected in series in a simple manner with a common, appropriately sized external thermostat. In this case it is essential that the metal jackets 10 of the reactors 1 can be controlled independently from each other. This is essential in case each reactor 1 is provided with its own third or intermediate thermostat.

Besides the calorimeter described above with reference to FIGS. 1A and 1B other calorimeters, which can be adapted to interact with two separate thermostats and allow the separation of the two heat balances can also be utilized for the determination of the heat capacity of a medium and the overall heat coefficient with the method of the invention.

Figure 2:
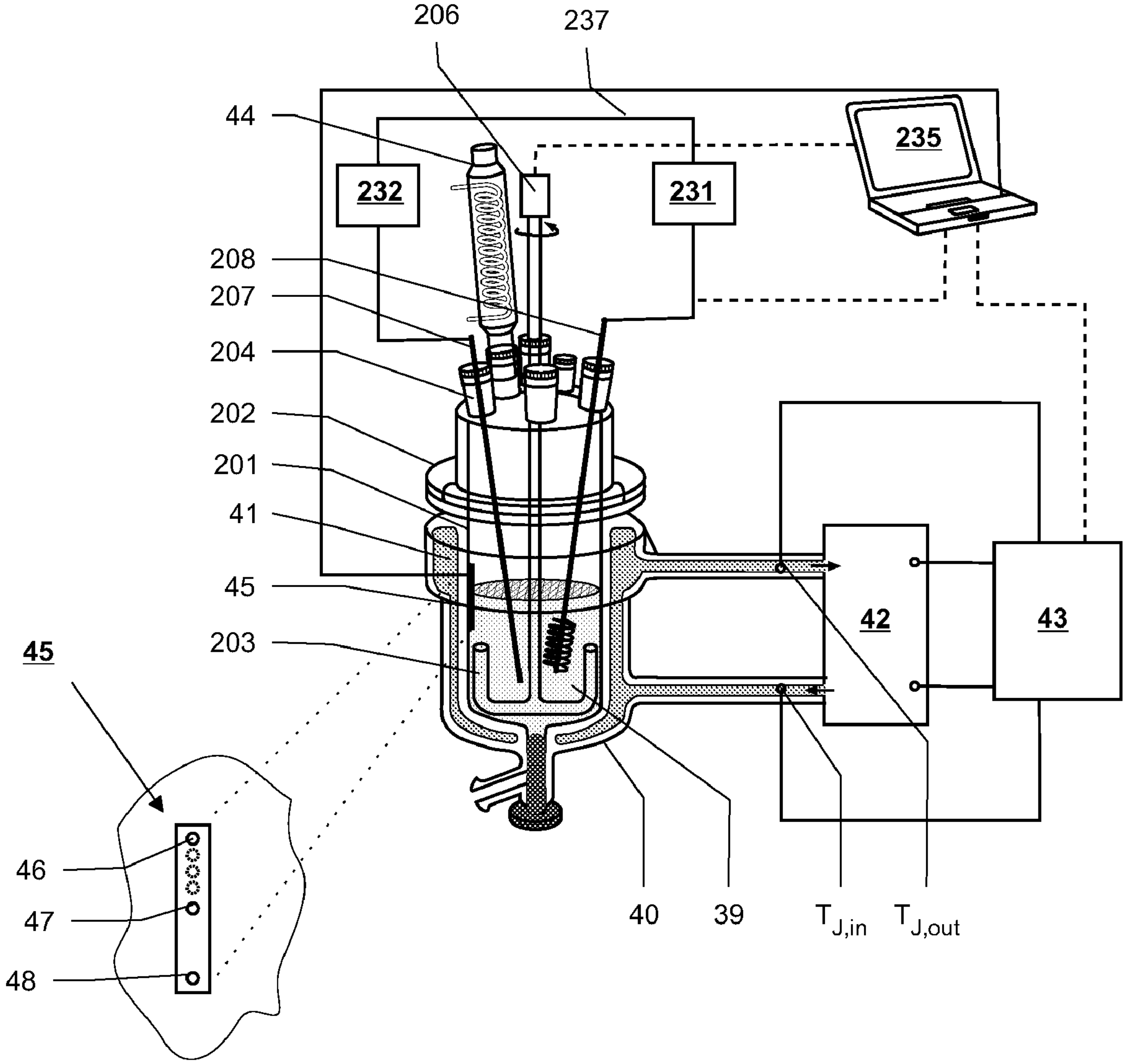
FIG. 2 shows a schematic view of a calorimeter with a first and second thermostat and an array of heat flux sensors as means for providing an outer heat balance and with an inset showing an enlarged view of said array.

Another suitable calorimeter setup is shown in FIG. 2. The calorimeter comprises a reactor 201 in which a medium 39 is arranged. A thermo-controlled jacket 40 surrounds the reactor 201. The jacket 40 is filled with a heat transfer fluid 41 as heat carrier. The temperature $T_J$ of the heat transfer fluid 41 is controlled with a heat exchanger 42, which is connected to a suitable controller 43. In order to monitor and control the temperature $T_J$ of the heat transfer fluid 41, the temperature $T_J$ of the heat transfer fluid 41 are determined from the difference of the temperatures measured with suitable temperature sensors at the inlet $T_{J,in}$ and outlet $T_{J,out}$ of the heat-exchanger 42. The jacket 40 filled with the heat transfer fluid 41, the heat exchanger 42 and the controller 43 constitute the second thermostat.

The calorimeter further comprises a removable lid 202 with several ports 204 for introducing for example a stirrer 203 connected to a stirrer drive 206, a first temperature sensor 207 for measuring the temperature $T_r$ inside the reactor, a compensation heater 208 being in contact with the medium 39 and a condenser 44. Additionally, there are further ports 204 e.g. for introducing the medium 39, adding further components or for further sensors and the like.

The compensation heater 208 and the first temperature sensor 207 are connected to a first control loop 237 comprising a power meter 231 and a temperature controller 232. These components constitute a first thermostat.

At the inner wall of the reactor 201 an array of heat flux sensors 45 is attached. This array 45 constitutes the means for providing an outer heat balance. It is shown in greater detail in the inset in FIG. 2. The array 45 comprises a linear arrangement of at least three heat flux sensors 46, 47, 48. The array 45 is partially immersed in the medium 39 in such a way, that at least the topmost heat flux sensor 46 has no contact with the medium 39, the middle sensor 47 is partially immersed, and the lowest sensor 48 is immersed in the medium 39. With the heat flow data from these sensors 46 to 48 it is possible to calculate the overall heat transfer coefficient UA. The array 45 can be a linear one as shown here, but could also comprise several rows of sensors. The array 45 should comprise at least three sensors, but can have more than that or even be designed as a continuous sensor band. The UA determination will gain accuracy with the number of sensors involved.

The data and information obtained at least by the first control loop 237, the controller 43, the stirrer 203 and the array 45 are fed into a central control unit 235, which is here presented as an external unit, but could also be an internal unit. The central control unit 235 is described in more detail with regard to FIG. 1.

Depending on the setup of the calorimeter the temperature, the heat flow and/or the power of the thermostats is monitored with respective sensors arranged in the calorimeter.

Determination of the Overall Heat Coefficient and of the Total Heat Capacity

The total heat capacity of a medium can be determined by combining a mathematical method with the application of a defined modulated energy profile to a medium arranged in a calorimeter, which can provide two separate heat balances, such as the calorimeters described in FIGS. 1 and 2, where the modulated energy profile can be applied by the first and/or the third thermostat.

For the calorimeter in FIG. 1 the overall heat coefficient UA is comprised in the outer heat balance, in particular in the power of cooling $q_{cool}$ $$q_{cool} = UA \cdot (T_r - T_J) \quad [1]$$

and $$UA = \frac{q_{cool}}{T_r - T_J} \quad [2]$$

which can be determined continuously or at predefined time intervals throughout the experiment. $q_{cool}$ can either be measured directly with heat flow sensors or can be determined from the energy which is exchanged between the second thermostat and the third thermostat via modeling the third thermostat, in particular the temperatures, the current and voltage over the Peltier elements, e.g. according to EP 1 184 649 A1. The specific heat of the medium can be determined independently from the overall heat transfer coefficient by combining the results of the two heat balances—the inner heat balance and the outer heat balance.

The specific heat capacity $c_p$ can be determined from the data of the applied modulated energy profile and the changes induced by said modulation, in particular the characteristics of the modulated energy profile, the temperature of the medium, and the heat and/or temperature profiles of the three thermostats.

As the temperature $T_r$ of the medium inside the reactor and the temperature $T_J$ of the surrounding jacket can be controlled independently from each other, two independent heat balances can be determined. A heat balance describes the differences between the energy or heat inflow and its outflow. The different terms taken into account for the determination of the heat capacity of the medium are summarized in the following table, for more details regarding the definition of the different terms see A. Zogg, U. Fischer, K. Hungerbühler, Ind. Chem. Res. 42 (2003), 767-776:

| | | |
|---|---|---|
| $q_R = r \cdot V \cdot (-\Delta H_R)$ | [W] | Power of reaction |
| $q_{comp} = I_{comp} \cdot U_{comp}$ | [W] | Power of the compensation heater |
| $q_{dos} = f \cdot C_{p,dos} \cdot (T_{dos} - T_r)$ | [W] | Power due to dosing |
| $q_{flow} = UA \cdot (T_r - T_J)$ | [W] | Power transfer through the reactor wall |
| $q_r^{acc} = C_{p,r} \cdot \frac{\partial T_r}{\partial t}$ | [W] | Accumulated power of the medium |
| $q_J^{acc} = C_{p,J} \cdot \frac{\partial T_J}{\partial t}$ | [W] | Accumulated power of the jacket |

-continued

| | | |
|---|---|---|
| $q_{cool} = q_{Pelt} - q_{ohm} + q_{loss,Pelt}$ $= I\alpha T_h - 0.5 \cdot I^2 \cdot R + K \cdot (T_h - T_1)$ | [W] | Power of cooling through the Peltier element |

An inner heat balance also referred to as the heat balance of the reactor comprises the difference between the accumulated power of the medium $q_r^{acc}$ and the power of the reaction $q_R$, said difference equals the difference between the power inflow due to the compensation heater $q_{comp}$, the stirrer $q_{stir}$ and the dosing $q_{dos}$ and the power outflow through the lid $q_{lid}$ and the reactor wall $q_{flow}$:

$$q_{comp}+q_{dos}+q_{stir}-q_{flow}-q_{lid}=q_r^{acc}-q_R \quad [3]$$

In the same manner an outer heat balance or an accumulated heat balance of the jacket $q_J^{acc}$ can be determined:

$$q_{flow}+q_{lid}-q_{loss}-q_{cool}=q_J^{acc} \quad [4]$$

The complete heat balance of the calorimeter is a combination of the inner and the outer heat balance:

$$q_{comp}+q_{dos}+q_{stir}-q_{cool}-q_{loss}=q_r^{acc}+q_J^{acc}-q_R \quad [5]$$

When a modulated energy profile is applied to the medium each of these terms can be written as a sum of steady state $\overline{X}_i$ and modulated terms $\tilde{X}_i$:

$$X_i=\overline{X}_i+\tilde{X}_i \quad [6]$$

With the assumption, that the modulated heat or energy profile provides only small changes, the power of the reaction $q_R$, power losses $q_{loss}$ as well as the power due to the stirrer $q_{stir}$ can be considered to be constants, which do not affect the modulated terms. The complete heat balance of the calorimeter $\tilde{q}_{acc}$ can be expressed as:

$$\tilde{q}_{acc} = \tilde{q}_R^{acc} + \tilde{q}_J^{acc} = C_{p,r}\frac{\partial T_R}{\partial t} + C_{p,J}\frac{\partial T_J}{\partial t} = \tilde{q}_{comp} - \tilde{q}_{cool} \quad [7]$$

For the calorimeter presented in the FIG. 1 the power variations due to temperature changes of the jacket are very small, usually below 0.02° C., therefore, the jacket accumulation term $\tilde{q}_J^{acc}$ can also be neglected.

For the determination of the specific heat $c_p$ of an unknown medium, the heat capacity of the reactor wall $C_{p,i}$ which can be determined by a commonly known calibration function, has to be subtracted. This leads to the following expression for the specific heat of the medium $c_p$, where m is the mass of the reactor medium:

$$c_p = \frac{C_{p,r} - C_{p,i}}{m} \quad [8]$$

With the calorimeter presented in FIG. 1 in combination with the described method for the $c_p$ determination several experiments were carried out with different modulated energy profiles.

For the calorimeter in FIG. 2 the overall heat coefficient UA can be calculated from the heat flows $q_1$, $q_2$ and $q_3$ obtained by the array of heat flux sensors, the temperature of the medium inside the reactor $T_r$ and the temperature of the fluid heat carrier $T_J=\Delta(T_{J,in}, T_{J,out})$, when the base area of the reactor $A_r$, its radius $R_r$ and the height of the sensors c are known. This can be expressed as follows:

$$h = \frac{q_3 - q_2}{q_1 - q_s}, \qquad [9]$$

$$A = A_r + 2\pi \cdot R_r \cdot c \cdot h \qquad [10]$$

and $$UA = \frac{q_{flowl}}{T_r - T_J}. \qquad [11]$$

The specific heat capacity of the medium $c_p$ can be determined from the data of the applied modulated energy profile and the changes induced by said modulation, in particular the characteristics of the modulated energy profile, the temperature of the medium, and the heat and/or temperature profiles of the first and second thermostats. The determination of the heat capacity $c_p$ with the calorimeter shown in FIG. 2 is similar to the determination with the calorimeter shown in FIG. 1, with the difference, that there is no third thermostat. The heat flow through the wall $q_{flow}$ can be measured directly with the arrangement of heat flow sensors. $q_{cool}$ is not applicable as the calorimeter presented in FIG. 2 does not comprise a third thermostat.

EXPERIMENTS

Several experiments were carried out, in particular with the calorimeter shown in FIG. 1. In these experiments the reactor and the jacket temperature are controlled by two separate PID controllers, such as the control loops 37 and 38 in FIG. 1. A modulated energy profile is applied to the medium as temperature modulation provided by the compensation heater. The reactor set-temperature is either superimposed by an oscillation or with a step function as modulation.

The modulated energy profile applied to the medium has an influence on the resulting reactor $T_r$ and jacket temperature $T_J$ as well as on the heating $q_{comp}$ and the cooling power $q_{cool}$. When the modulated energy profile is provided as a temperature modulation the resulting temperature and power signals will exhibit and follow the same or a similar type of modulation. The amplitudes and phases of each signal $T_r$, $T_J$, $q_{comp}$ and $q_{cool}$ can be calculated from the collected signals by applying a fit to the signals, here a cosine function. This kind of mathematical signal optimization is well known and therefore not described in detail.

Example 1

In a first experiment the reactor was filled with 34 ml of water. The jacket temperature $T_J$ was set to 17° C. and the temperature of the heat exchanger to 15° C. Both temperatures were kept at a constant value throughout the experiments. The stirrer speed was 500 rpm.

The reaction temperature $T_r$ was superimposed with a modulated energy profile in form of an oscillating set-temperature provided by the compensation heater. This modulation resulted in a reaction temperature profile of $$T_r = 25 + 0.5 \cdot \cos\left(\frac{t}{120}\right)[°C.], \qquad [12]$$

with t being the time constant expressed in seconds [s]. This modulated temperature profile corresponds to an oscillating period of about 2 min and an amplitude of about ±0.5° C. The amplitude can vary slightly due to a delay in the response time of the temperature controller of the compensation heater. In the case of the calorimeter described in FIG. 1 it equals about ±0.52° C.

For simulating a reaction and providing a power due to dosing additional water was added after 48 min from the start of the experiment with a flow rate of 0.125 ml/min until a total volume of 50.5 ml was reached after 180 min.

During the experiment the total and the specific heat capacity as well as the overall heat coefficient have been calculated every 12 min, which can also be calculated at different time intervals or even continuously.

The superposition of the reaction temperature $T_r$ with the sinusoidal energy profile allows the determination of $C_{p,r}$. The oscillating behavior of $T_r$ can also be observed in the reactor temperature and the cooling power, which follow this behavior. By determining the amplitude and the phase of each of the three oscillating signals—the heat or temperature of the compensation heater, the temperature of the medium and the cooling power—it is possible to calculate the heat capacity of the medium $C_{p,r}$ with a greater accuracy than with a classical double walled reactor as the measurement of the cooling power is more accurate due to the homogeneity of the constantly stirred medium and the innovative temperature control of the second and third thermostat.

An oscillating modulation applied here as a modulated energy profile can be generally expressed as:

$$\overline{X}_i = \Delta X_i \cos(\omega \cdot t + \phi_i) \qquad [13]$$

This oscillating modulation can be implemented in the expression for the complete heat capacity (see equation 7):

$$C_{p,r}\frac{\partial(\Delta T_r \cos(\varpi \cdot t + \varphi_r))}{\partial t} = \Delta q_{comp}\cos(\varpi \cdot t + \varphi_{comp}) - \Delta q_{cool}\cos(\varpi \cdot t + \varphi_{cool}) \qquad [14]$$

When $\phi_{comp}$=0 rad and t=0 s equation 13 can be rearranged to:

$$C_{p,r} = \frac{\Delta q_{comp} - \Delta q_{cool} \cdot \cos(\varphi_{cool})}{-\omega \cdot \Delta T_r \cdot \sin(\varphi_r)}[J/K] \qquad [15]$$

The term $C_{p,r}$ incorporates the total heat capacity of medium $C_{p,m}$=m·$c_p$ as well as the heat capacity of the stirrer, the heater, and the heat capacity of a part of the reactor $C_{p,i}$. $C_{p,i}$ is calibrated using an optimization function, which determines the best correlation between $C_{p,i}$ and a set of experimental parameters which contribute to the heat balance such as $T_J$, $T_r$, $q_{cool}$ and $q_{comp}$. The calibration function is the difference between the calculated total $C_{p,r}$ and the $C_{p,m}$ of the medium. This calibration function can be easily calculated using a medium of known heat capacity and can be utilized for media with unknown heat capacities.

For the determination of the specific heat of an unknown medium $c_p$ the heat capacity of the reactor wall, as given by the above described calibration function, has to be subtracted. This leads to the following expression for the specific heat of the medium $c_p$, where m is the mass of the reactor medium:

$$c_p = \frac{C_{p,r} - C_{p,i}}{m}[J/g \cdot K] \qquad [8]$$

An analogous experiment was carried out with ethanol as medium.

Figure 3:
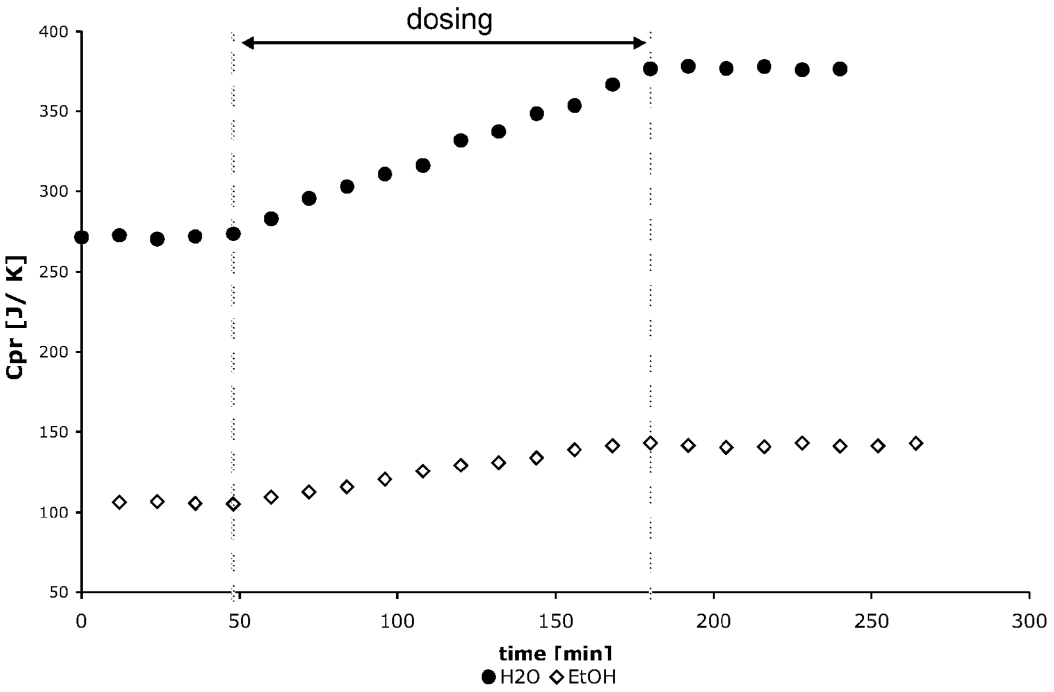
FIG. 3 is a diagram showing the total heat capacity $C_{p,r}$ corresponding to the total heat capacity of the medium and of the reactor wall for water (●) and for ethanol (◇) determined from an experiment with the FIG. 1 calorimeter where an oscillating modulated energy profile is applied to the medium.
Figure 4:
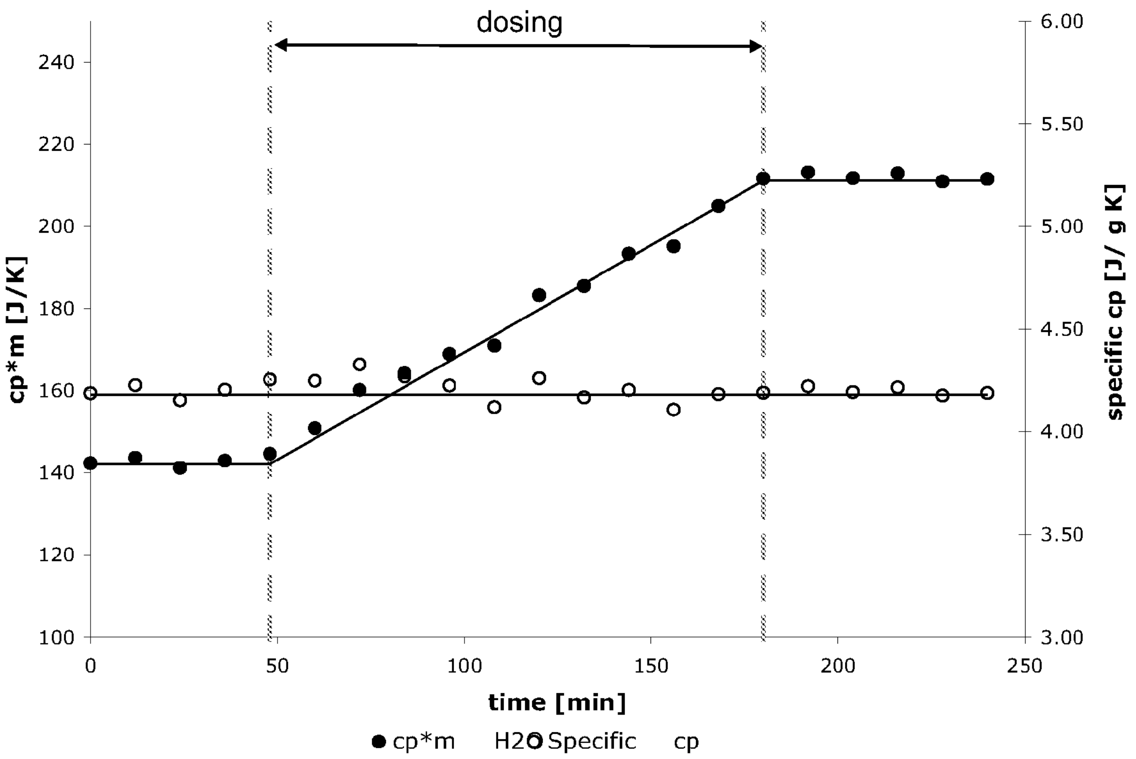
FIG. 4 is a diagram showing the total (●) and specific (○) heat capacity of water determined from the values shown in FIG. 3 with the plain lines representing the theoretical values.
Figure 5:
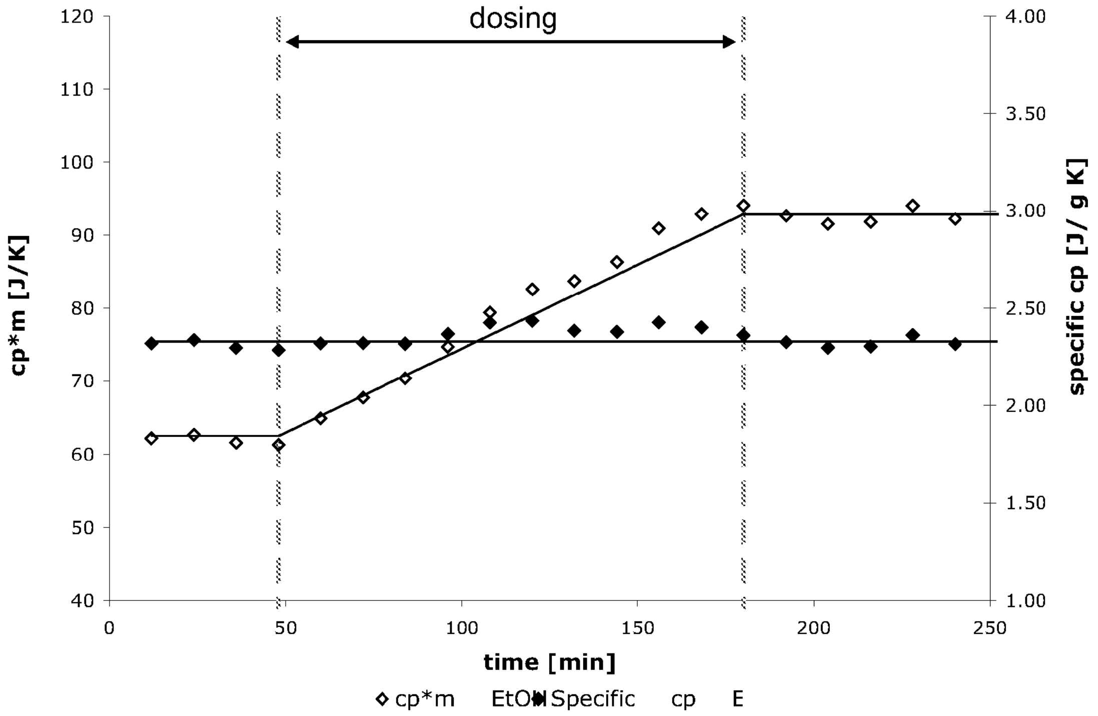
FIG. 5 is a diagram showing the total (◇) and specific (♦) heat capacity of ethanol determined from the values shown in FIG. 3 with the plain lines representing the theoretical values.

The results of these two experiments are shown in FIGS. 3, 4 and 5. FIG. 3 shows the changes in the total heat capacity $C_{p,r}$ for water ($H_2O$, ◇) and ethanol (EtOH, ●), respectively. $C_{p,r}$ was calculated according to equation 14.

The diagram of FIG. 4 shows the total (●) and the specific (○) heat capacity of water and FIG. 5 the total (◇) and the specific (♦) heat capacity of ethanol, respectively, which were determined according to equation 15. The plain lines represent the theoretical values of the total and the specific heat capacity for the two reaction media, respectively.

Example 2

In a second experiment the reactor was first filled with 25 ml of water and the temperature of the reactor $T_r$ was set to 25° C. A step function was then applied to the compensation heater $q_{comp}$ as modulated energy profile. Each step comprised an increase in reaction temperature $T_r$ of 0.8° C. and lasted for about 10 minutes.

The jacket temperature $T_J$ was set to 20° C. and the temperature of the heat exchanger to 10° C. After 60 min, water was added with a flow rate of 0.125 ml/min until a total volume of 50 ml was reached after 260 min. The stirrer speed was set to 500 rpm.

The total heat capacities have been calculated every 20 minutes.

In case of the step function, the modulation can be expressed as:

$$\tilde{X}_i = X_{i,0} + \sum_{n=1}^{j} B_{i,n}\exp(-\lambda_{i,n} \cdot t) \quad [16]$$

where j is the order of the signal i. It could be determined experimentally that for the calorimeter and the experiment described above the order equals j=1 and equation 16 can be rewritten as:

$$\overline{X}_i = X_{i,0} + B_{i,1}\exp(-\lambda_{i,1} \cdot t) \quad [17]$$

As the step function is applied to $q_{comp}$ the order of $q_{comp}$ equals 0. Equation 17 is then incorporated into equation 7 leading to:

$$C_{p,r}\frac{d\left(\begin{matrix} T_0 + T_1\exp \\ (-\lambda_{T,1} \cdot t) \end{matrix}\right)}{dt} = C_{p,r} \cdot (-\lambda_{T,1}) \cdot T_1\exp(-\lambda_{T,1} \cdot t) = q_{comp,0} - (q_{cool,0} + q_{cool,1}\exp(-\lambda_{cool,1} \cdot t)) \quad [18]$$

Because of $$\lim_{t\to\infty}(\exp(-t)) = 0,$$

it can be concluded that $q_{comp,0}$ equals $q_{cool,0}$ which results in:

$$C_{p,r} \cdot (-\lambda_{T,q}) \cdot T_1 \cdot \exp(\lambda_{T,1}) = -q_{cool,1}\exp(\lambda_{cool,1}) \quad [19]$$

$$C_{p,r} = \frac{-q_{cool,1}\exp(\lambda_{cool,1})}{(-\lambda_{T,1}) \cdot T_1 \cdot \exp(\lambda_{cool,1})}[J/K] \quad [20]$$

$$c_p = \frac{C_{p,r} - C_{p,i}}{\mathrm{m}}[J/g \cdot K] \quad [21]$$

The total heat capacity of the medium and the reactor wall can be determined according to equation 20 and the total and the specific heat capacity for the medium can then be determined according to equation 8.

An analogous experiment was carried out with ethanol as medium. The results of these two experiments are shown in FIGS. 6, 7 and 8.

Figure 6:
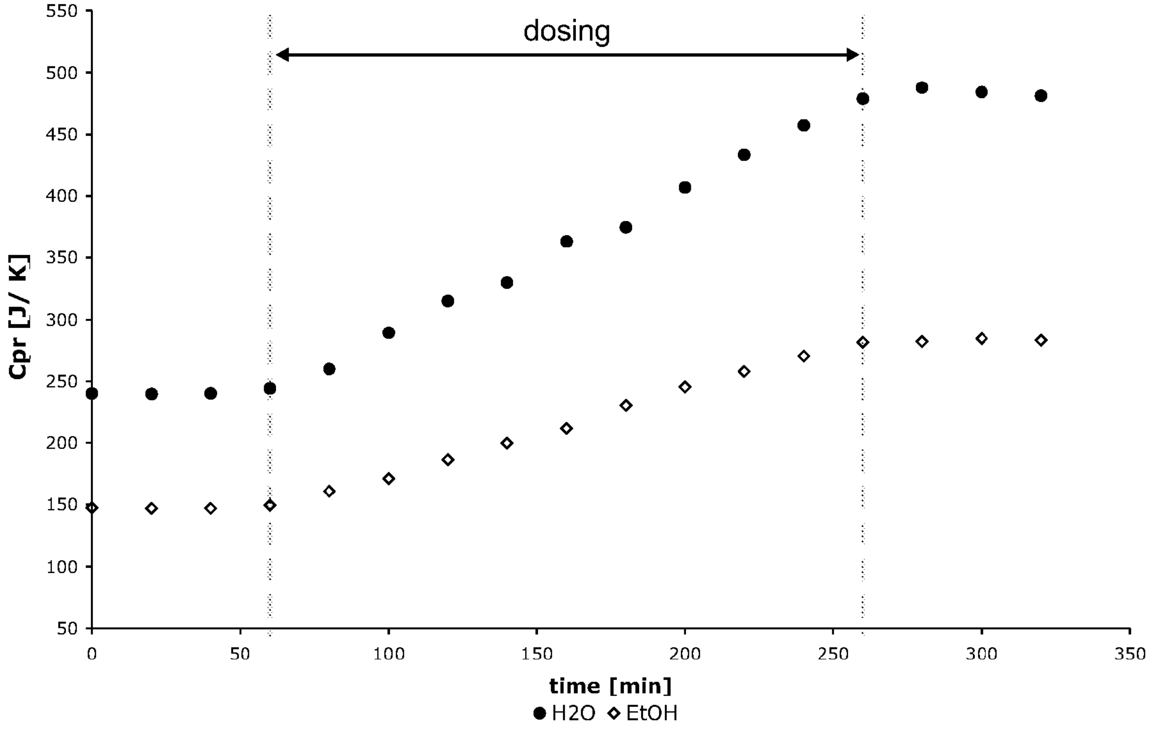
FIG. 6 is a diagram showing the total heat capacity $C_{p,r}$ corresponding to the total heat capacity of the medium and of the reactor wall determined for water (●) and for ethanol (◇) determined from an experiment with the calorimeter of FIG. 1 where a stepwise modulated energy profile is applied to the medium.

FIG. 6 shows the changes in the total heat capacity $C_{p,r}$ for water (◇) and ethanol (●), respectively, as medium. $C_{p,r}$ was calculated according to equation 20.

Figure 7:
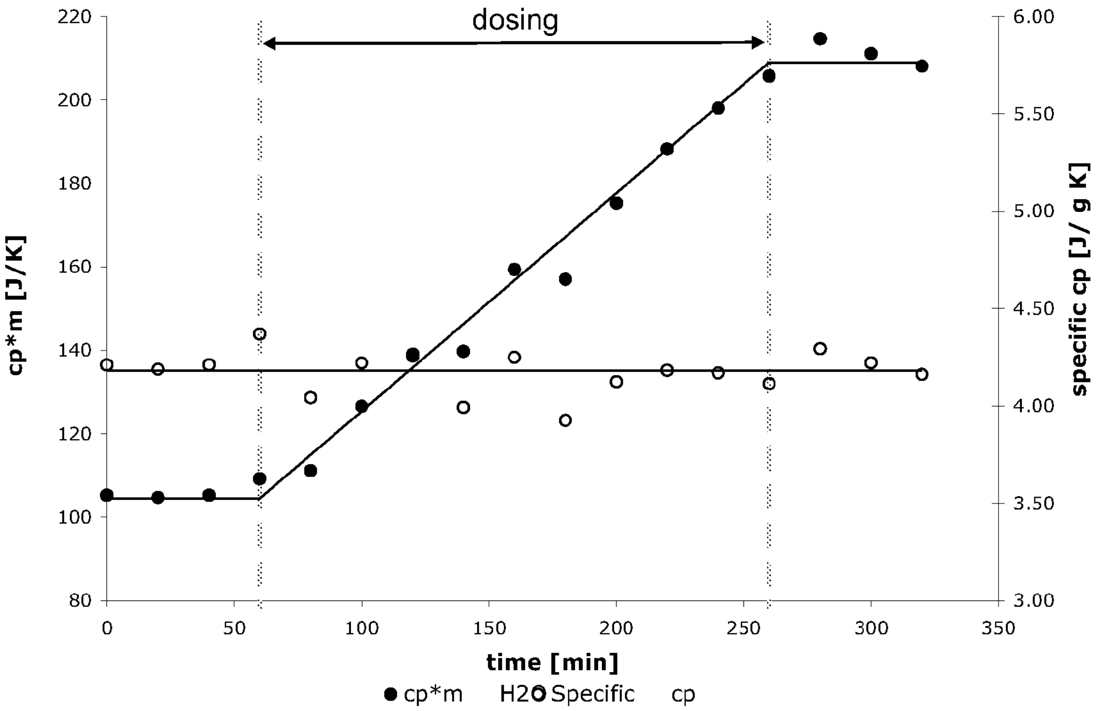
FIG. 7 is a diagram showing the total (●) and specific (○) heat capacity of water determined from the values shown in FIG. 6 with the plain lines representing the theoretical values.
Figure 8:
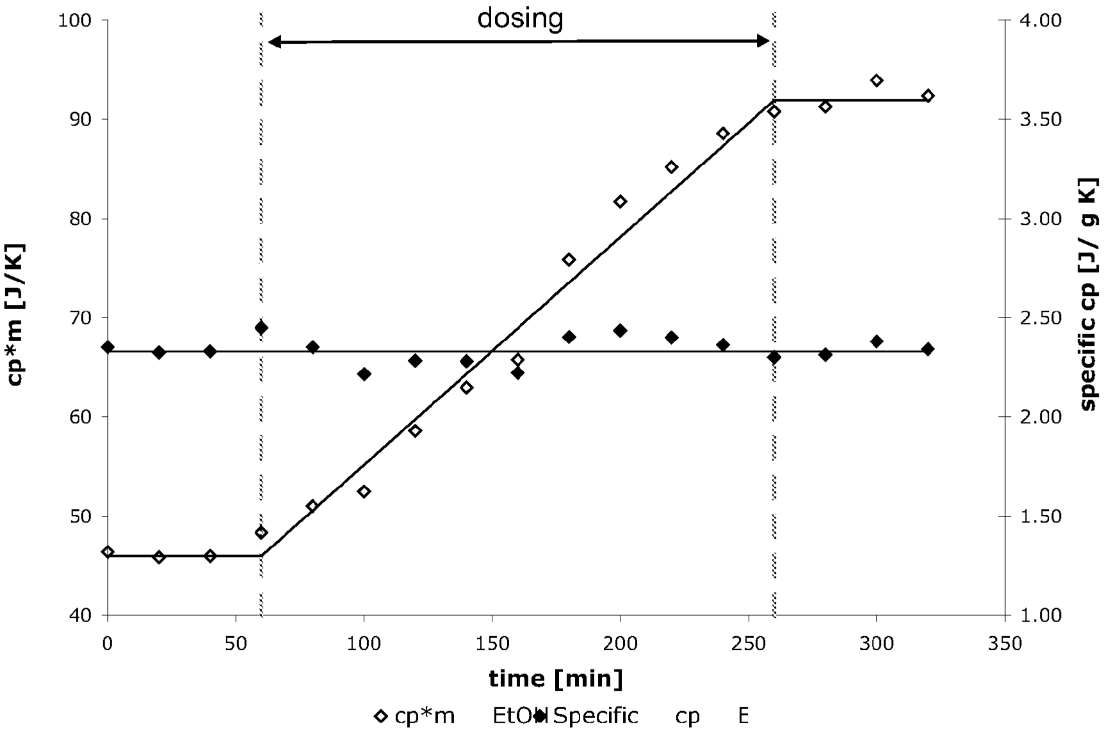
FIG. 8 is a diagram showing the total (◇) and specific (♦) heat capacity of ethanol determined from the values shown in FIG. 6 with the plain lines representing the theoretical values.

The diagram of FIG. 7 shows the total (●) and the specific (○) heat capacity of water and FIG. 8 the total (◇) and the specific (♦) heat capacity of ethanol, respectively, which were determined according to equation 15 by subtracting the pre-calibrated heat capacity of the reactor wall. The heat capacity of the reactor wall is a specific parameter, which depends on the design and material of the reactor and is usually already specified by the producer of the reactor or can be determined experimentally. The plain lines represent the theoretical values for the two reaction media.

What is claimed is:

1. A method for determining the specific heat capacity of a medium with a calorimeter that comprises a reactor, a stirrer, a first thermostat for providing an inner heat balance, a second thermostat, a means for providing an outer heat balance and a central control unit, the method comprising the steps of:

applying a modulated energy profile to the medium, which is arranged inside the reactor under near isothermal conditions;

monitoring the energy changes that result from applying the energy profile, as a function of time, of at least one of: the medium, the reactor, the first thermostat, the second thermostat and the means for providing the outer heat balance;

determining the inner and outer heat balances, independently from each other at predefined time intervals; and calculating, from the inner and outer heat balances, an overall heat transfer coefficient and the specific heat capacity of the medium, simultaneously and independently from each other, as a function of time.

2. The method of claim 1, wherein:

the means for providing the outer heat balance comprises an array of heat flux sensors arranged inside the reactor.

3. The method of claim 1, wherein:

the modulated energy profile is applied as a periodic or as a stochastic modulation.

4. The method of claim 1, wherein:

the applying step comprises the step of superimposing energy provided by the first thermostat with the modulated energy profile.

5. The method of claim 1, wherein:

the monitoring step comprises monitoring at least one of the phase and the amplitude of the resulting energy change of at least one of: the medium, the reactor, the first thermostat, the second thermostat and the means for providing the outer heat balance.

6. The method of claim 5, wherein:

the modulation of energy profile is selected from the group consisting of: a sinusoidal modulation, a rectangular modulation, a single pulse, multiple pulses and a ramp.

7. The method of claim 1, wherein:

the means for providing the outer heat balance comprises a third thermostat, in thermal contact with the second thermostat, the third thermostat generating the applied modulated energy profile.

8. The method of claim 7, wherein:

the applying step comprises the step of maintaining near isothermal conditions by controlling the first thermostat to compensate for the heat provided by at least one of: the second thermostat, the third thermostat and the medium.

9. The method of claim 7, wherein:

the modulated energy profile is applied as one of: a modulated power profile, a modulated heat flow profile or a modulated temperature profile.

10. The method of claim 9, wherein:

the resulting energy change is determined by at least one of: at least one temperature sensor, at least one power meter and at least one heat flow sensor.

11. A calorimeter for determining the specific heat capacity of a medium, comprising:

a reactor;

a sensor;

a first thermostat for providing an inner heat balance;

a second thermostat;

a means for providing an outer heat balance, such that a modulated energy profile is provided to the medium by at least one of: the first thermostat and the means for providing the outer heat balance;

a stirrer arranged inside the reactor; and a control unit, comprising a program with an algorithm to:

determine, using data obtained from the sensor as a function of time, the energy changes resulting from the modulated energy profile to at least one of: the medium, the reactor, the first thermostat, the second thermostat and the means for providing the outer heat balance;

determine an inner and an outer heat balance, and determine simultaneously and independently the specific heat capacity of the medium and the overall heat transfer coefficient as a function of time.

12. The calorimeter of claim 11, wherein:

the first thermostat comprises:

a compensation heater, a first temperature sensor arranged inside the reactor; and a first temperature controller.

13. The calorimeter of claim 11, wherein:

the means for providing the outer heat balance comprises:

an arrangement of at least three heat flux sensors, the arrangement being arranged in contact with an inner wall of the reactor and being at least partially immersed in the medium arranged inside the reactor.

14. The calorimeter of claim 11, wherein:

the second thermostat comprises:

a fluid heat carrier arranged in a jacket surrounding the reactor; and a heat exchange unit.

15. The calorimeter of claim 11, wherein:

the means for providing the outer heat balance comprises a third thermostat, thermally connected to the second thermostat, the third thermostat comprising:

a third temperature controller;

a heating/cooling unit, a solid heat carrier in thermal contact with the reactor; and a second temperature sensor for measuring the temperature inside the heat carrier.

16. The calorimeter of claim 15, wherein:

the third thermostat provides a modulated energy profile to the medium.

17. A computer program, embodied on a computer-readable medium, designed to calculate the overall heat coefficient and the specific heat capacity of a medium from data that are obtained while applying the method of claim 1 to a medium arranged inside a reactor of a calorimeter, the calorimeter being adapted to independently provide at least an inner heat balance and an outer heat balance.

* * * * *

UNITED STATES PATENT AND TRADEMARK OFFICE

CERTIFICATE OF CORRECTION

PATENT NO. : 7,712,956 B2
APPLICATION NO. : 12/372003
DATED : May 11, 2010
INVENTOR(S) : Richner et al.

It is certified that error appears in the above-identified patent and that said Letters Patent is hereby corrected as shown below:

On the title page, Item (75) Inventors, line 1, please delete “Zurich” and insert -- Zuerich --.

In column 12, line 28, please delete “ $\overline{X}_i = \Delta X_i \cos(\omega \cdot t + \varphi_i)$ ” and insert -- $\tilde{X}_i = \Delta X_i \cos(\omega \cdot t + \varphi_i)$ --.

In column 13, line 41, please delete “ $\overline{X}_i = X_{i,0} + B_{i,1} \exp(-\lambda_{i,1} \cdot t)$ ” and insert -- $\tilde{X}_i = X_{i,0} + B_{i,1} \exp(-\lambda_{i,1} \cdot t)$ --.

Signed and Sealed this

Tenth Day of August, 2010

David J. Kappos
*Director of the United States Patent and Trademark Office*